(12) United States Patent
Cho

(10) Patent No.: US 9,833,580 B2
(45) Date of Patent: Dec. 5, 2017

(54) MEDICAL HEATING DEVICE HAVING MEANS FOR BLOCKING FLOW OF FLUID

(71) Applicant: Yong Il Cho, Seoul (KR)

(72) Inventor: Yong Il Cho, Seoul (KR)

( * ) Notice: Subject to any disclaimer, the term of this patent is extended or adjusted under 35 U.S.C. 154(b) by 143 days.

(21) Appl. No.: 14/759,446

(22) PCT Filed: Dec. 17, 2013

(86) PCT No.: PCT/KR2013/011712
§ 371 (c)(1),
(2) Date: Jul. 7, 2015

(87) PCT Pub. No.: WO2014/178512
PCT Pub. Date: Nov. 6, 2014

(65) Prior Publication Data
US 2016/0045679 A1    Feb. 18, 2016

(30) Foreign Application Priority Data

May 3, 2013  (KR) .................. 10-2013-0050172

(51) Int. Cl.
| | | |
|---|---|---|
| A61M 5/44 | (2006.01) | |
| A61M 1/02 | (2006.01) | |
| A61M 1/36 | (2006.01) | |
| A61M 5/36 | (2006.01) | |
| A61M 5/38 | (2006.01) | |
| A61M 5/40 | (2006.01) | |
| A61M 39/24 | (2006.01) | |

(52) U.S. Cl.
CPC ............ *A61M 5/44* (2013.01); *A61M 1/0281* (2013.01); *A61M 1/3627* (2013.01); *A61M 5/36* (2013.01);
(Continued)

(58) Field of Classification Search
CPC .......... A61M 5/44; A61M 5/385; A61M 5/36; A61M 1/0281; A61M 1/3627; A61M 5/40;
(Continued)

(56) References Cited

U.S. PATENT DOCUMENTS

| 4,309,592 A | 1/1982 | Le Boeuf | |
|---|---|---|---|
| 2010/0222740 A1* | 9/2010 | Park | A61M 5/44 604/114 |

FOREIGN PATENT DOCUMENTS

| CN | 101180016 | 5/2008 |
|---|---|---|
| CN | 102105188 | 6/2011 |

(Continued)

OTHER PUBLICATIONS

State Intellectual Property Office of the People's Republic of China, Office Action of the corresponding Chinese Patent Application No. 201380072548.0 dated Jun. 3, 2016.
(Continued)

*Primary Examiner* — Bhisma Mehta
*Assistant Examiner* — Hamza Darb
(74) *Attorney, Agent, or Firm* — LEX IP MEISTER, PLLC

(57) ABSTRACT

A heating device for blocking flow of air if the inside of a cartridge enters a negative-pressure state is provided. The device includes a cartridge upper plate having a fluid-guide member for guiding the flow of a fluid; a cartridge lower plate having an inlet, an outlet and another fluid-guide member positioned spaced apart from the fluid-guide member of the cartridge upper plate; a heater disposed between the cartridge upper plate and the lower plate and heating the fluid being guided by the fluid-guide members; air filters positioned outside the fluid-guide members and discharging air bubbles in the heated fluid into the atmosphere; and extension units which are provided on the cartridge upper and lower plates having film members and outflow and discharge passages and that keep the flow of fluid normal in the positive-pressure state and block the fluid movement pathway if a negative pressure occurs inside the cartridge.

6 Claims, 9 Drawing Sheets

(52) U.S. Cl.
CPC ............... *A61M 5/385* (2013.01); *A61M 5/40* (2013.01); *A61M 2039/2406* (2013.01); *A61M 2205/127* (2013.01); *A61M 2205/36* (2013.01); *A61M 2205/3653* (2013.01)

(58) Field of Classification Search
CPC .. A61M 2039/2406; A61M 2205/3653; A61M 2205/127; A61M 2205/36
See application file for complete search history.

(56) References Cited

FOREIGN PATENT DOCUMENTS

| | | |
|---|---|---|
| EP | 1525400 | 1/2004 |
| EP | 2140892 | 1/2010 |
| EP | 2311514 | 4/2011 |
| JP | 2004-215758 | 8/2004 |
| JP | 2004-337353 | 12/2004 |
| KR | 10-1984-0006769 | 12/1984 |
| KR | 10-2003-0028815 | 4/2003 |
| KR | 10-0553129 | 2/2006 |
| KR | 10-1012535 | 2/2011 |
| KR | 10-2012-0081543 | 7/2012 |
| WO | 2012/096468 | 7/2012 |

OTHER PUBLICATIONS

European Patent Office, search report of the corresponding EP Patent Application No. 13883578.0 dated Jul. 22, 2016.
International Search Report and Written Opinion, Feb. 20, 2014, PCT/KR2013/011712.

\* cited by examiner

MEDICAL HEATING DEVICE HAVING MEANS FOR BLOCKING FLOW OF FLUID

TECHNICAL FIELD

The present invention relates to a medical heating apparatus, and more particularly, to a medical heating apparatus including means for blocking a flow of a fluid, wherein the inside and outside of a cartridge are automatically blocked by negative pressure when pressure within the cartridge of the medical heating apparatus for heating and supplying a infusion solution or blood changes from a positive pressure state to a negative pressure state.

BACKGROUND ART

When a infusion solution or blood is injected into a patient, the infusion solution or blood is warmed by means for making the infusion solution or blood not have a temperature difference with a body temperature as much as possible.

If a infusion solution or blood that is stored in a low temperature state in order to prevent the infection of a virus is directly injected into a patient, the patient may be in a dangerous situation.

Accordingly, a heating apparatus is used as means for raising the temperature of a infusion solution or blood so that the infusion solution or blood has almost the same temperature as a body temperature when it is injected into the human body.

Such a heating apparatus includes a PCB type of heater disposed within a cartridge which raises the temperature of a infusion solution or blood in such a manner that the infusion solution or blood passes around the PCB type of heater.

However, if a infusion solution or blood is warmed through the heating apparatus, bubbles may be generated in the infusion solution or blood, and the generated bubbles within the infusion solution or blood may be injected into the human body.

An air filter capable of blocking the discharge of a fluid and discharging only a gas is installed in the cartridge as means for removing bubbles that may be generated when a infusion solution or blood is warmed.

A heating apparatus of Korean Patent No. 10-1012535 includes: a heater; a barrier rib and a cover member that are respectively disposed on front and rear surfaces of the heater and that form a passage so that a fluid moves while surrounding the heater; an air filter unit that is disposed on the passage and that removes air; a first connection unit through which a fluid flows to the passage; and a second connection unit through which the fluid flows from the passage.

Such a heating apparatus can warm a infusion solution or blood and discharge bubbles that may be generated in a heating process to the outside of the cover member.

DISCLOSURE

Technical Problem

In the heating apparatus of the patent document, pressure within the cover member substantially increases because a temperature within the cover member rises when a temperature on the passage side formed of the cover members rises in the heating process.

If the pressure within the cover member increases and becomes a positive pressure, bubbles generated within the cover member exit outside the cover member through the air filter unit in a process of supplying a infusion solution or blood. Accordingly, the bubbles are not injected into the human body.

However, if the infusion solution or blood is fully injected into the human body or if the supply of the infusion solution or blood is stopped during use, the pressure that increased within the cover member is lowered. Accordingly, there is a possibility that a phenomenon in which the air flows backward to the inside of the cover member may occur because the inside of the cover member enters a negative pressure state and thus atmospheric pressure is substantially higher than pressure within the cover member.

If the air flows into the cover member, a fatal result may be caused because the air may flow into the blood vessel of the human body.

Furthermore, in order to inject a infusion solution or blood into the human body, a vessel in which a infusion solution is contained or a vessel in which blood is contained needs to be installed at a location higher than the human body. If the vessel is placed at a location lower than the human body due to surrounding environments or a physical cause, a phenomenon in which a supplied infusion solution or blood may flow backward may occur.

A scheme capable of overcoming such problems has not been prepared in the heating apparatus of the patent document.

The present invention has been invented to solve the problems of the conventional art, and an object of the present invention is to provide a medical heating apparatus including means capable of heating a infusion solution or blood, preventing a infusion solution or blood from flowing backward even if the inside of a cartridge changes to a negative pressure state, and also blocking a flow of a fluid so that outside air does not flow therein.

Technical Solution

A heating apparatus for accomplishing the object of the present invention includes: an upper plate of a cartridge in which an inlet is formed and fluid guide members for guiding a flow of a fluid are formed;

a lower plate of the cartridge in which an outlet is formed and other fluid guide members spaced apart from the fluid guide members at an interval are formed;

a heater which is disposed between the upper and lower plates of the cartridge and which heats the fluid guided by the fluid guide members;

an air filter which is placed outside the fluid guide members and discharges air bubbles generated in the heated fluid to atmosphere; and means provided on fluid flow passages of the upper and lower plates of the cartridge that normally maintain a flow of the fluid in a positive pressure state, and block the moving passage of the fluid when negative pressure is generated within the cartridge.

The fluid flow blocking means provided by the present invention includes:

an extension unit which is formed in the upper plate of the cartridge and through which the fluid introduced through the fluid guide members passes;

a film member which is formed in the extension unit of the upper plate of the cartridge and closely attached to outsides of outflow passages through which the fluid is able to pass, and a discharge passage which discharges the fluid drained from the outflow passages;

an extension unit which is formed in the lower plate of the cartridge and through which the fluid introduced through the fluid guide members passes; and a region formed in the extension unit of the lower plate of the cartridge and that communicates with the outlet while communicating with the discharge passage.

Advantageous Effects

When blood or a infusion solution is warmed by a heater and started to be supplied and the inside of a cartridge enters a positive pressure state, the medical heating apparatus according to the present invention can normally supply a fluid while discharging air bubbles and preventing infusion solution from being discharged. On the contrary, when the supply of blood or a infusion solution is stopped or completed and the inside of the cartridge enters a negative pressure state, the medical heating apparatus according to the present invention blocks a flow of a fluid. Accordingly, external air can be prevented from flowing into the human body, and a supplied infusion solution or blood can be prevented from flowing backward.

MODE FOR INVENTION

Hereinafter, a medical heating apparatus according to preferred embodiments of the present invention are described in more detail with reference to the accompanying drawings.

Figure 1:
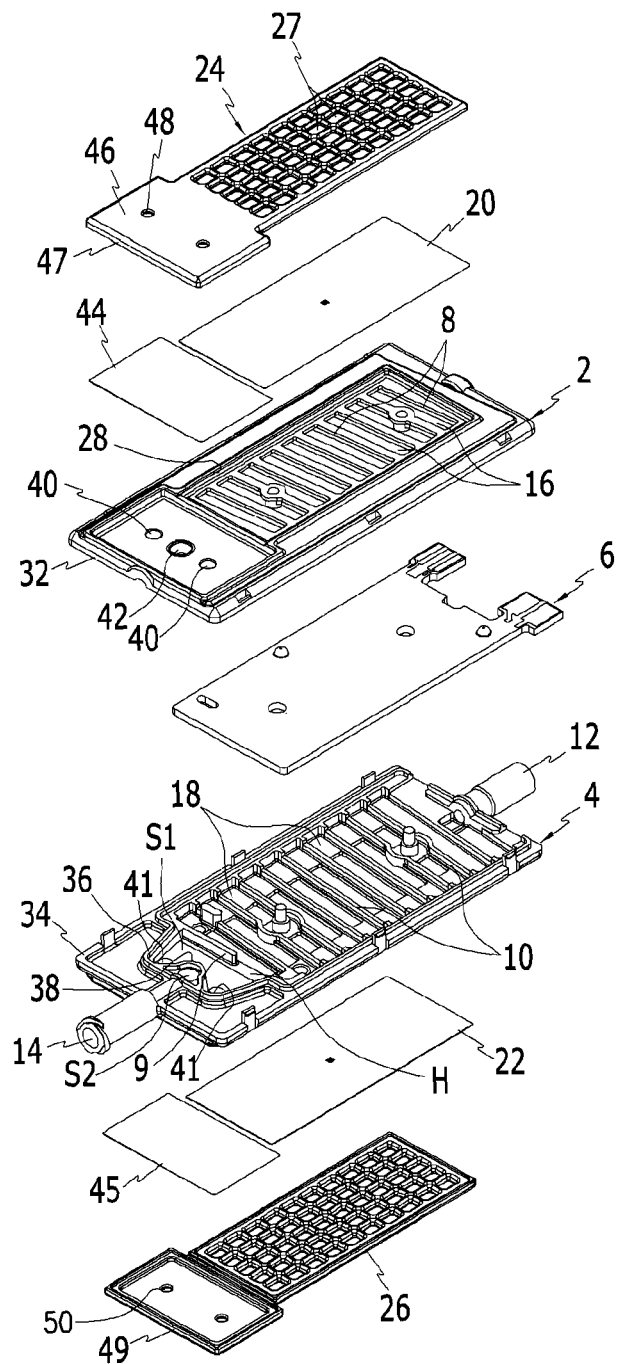
FIG. 1 is an exploded perspective view of a heating apparatus in accordance with an embodiment of the present invention, and is a diagram illustrating the upper plate of a cartridge in the direction in which the inside of the upper plate is viewed.
Figure 2:
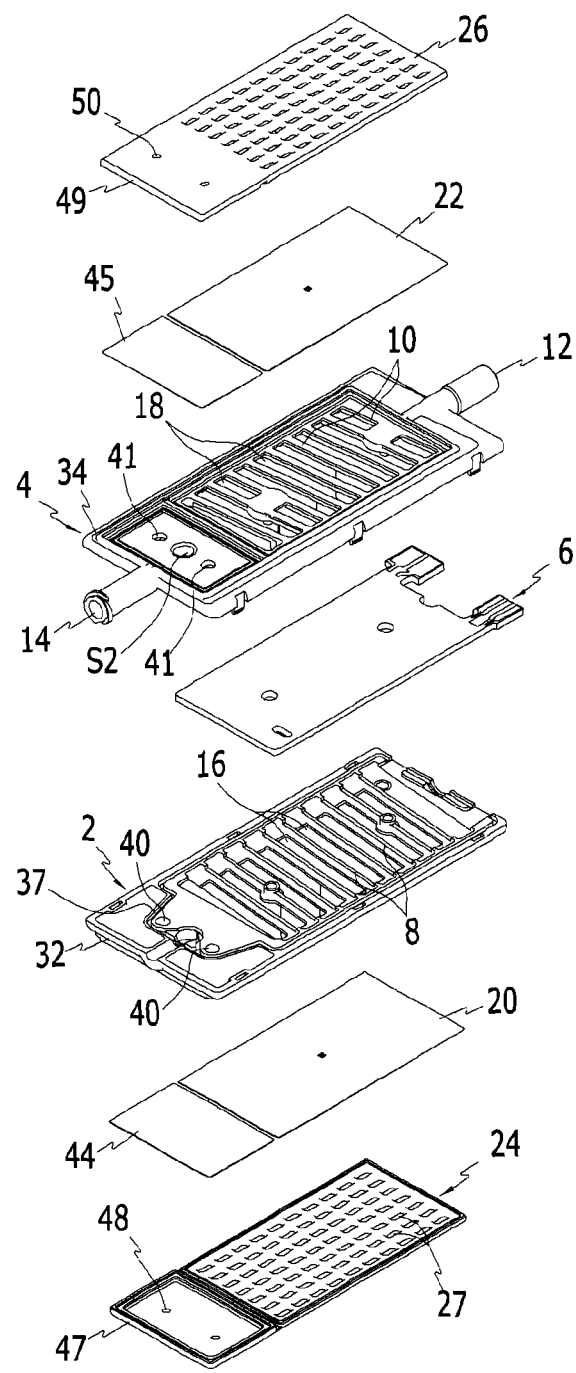
FIG. 2 is an exploded perspective view of a heating apparatus in accordance with an embodiment of the present invention and is a diagram illustrating the upper plate of a cartridge in the direction in which the inside of the lower plate is viewed.
Figure 3:
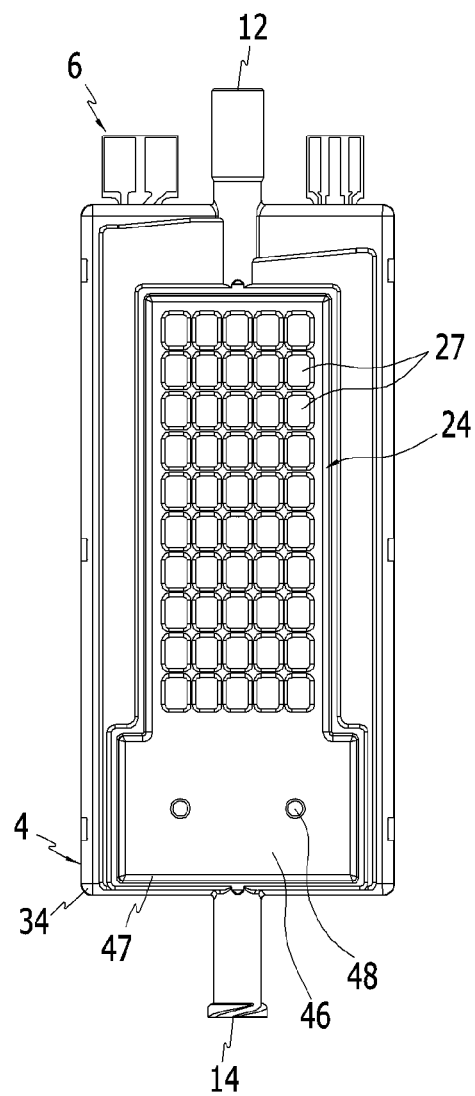
FIG. 3 is a plan view illustrating the state in which the heating apparatus in accordance with an embodiment of the present invention has been combined.

FIG. 1 is an exploded perspective view of a heating apparatus in accordance with an embodiment of the present invention, and FIG. 2 is a plan view illustrating the state in which the heating apparatus in accordance with an embodiment of the present invention has been coupled. Reference numeral 2 denotes the upper plate of a cartridge.

The upper plate 2 of a cartridge is made independently of a lower plate 4 of the cartridge, and the upper and lower plates form a single cartridge by adhesives, etc. The upper and lower plates of the cartridge described in the present embodiment are named thus for convenience of description, and the upper plate and the lower plate of the cartridge may be exchangeably named.

A heater 6 for heating a infusion solution or blood (hereinafter called a fluid) to a constant temperature when the fluid flows is installed between the upper plate 2 of the cartridge and the lower plate 4 of the cartridge.

The heater 6 may be a flat type of heater of a PCB type, and such a heater may be the same as or similar to commonly used heaters.

A plurality of fluid guide members 8 and 10 are respectively formed in the upper and lower plates 2 and 4 of the cartridge so that a fluid can flow between the upper plate 2 of the cartridge and the heater 6 and between the lower plate 4 of the cartridge and the heater 6.

The fluid guide members 8 formed in the upper plate 2 and the fluid guide members 10 formed in the lower plate 4 are slantedly formed in opposite directions in the front and rear surfaces of the heater 6, as illustrated in FIG. 1.

In such a structure, the fluid guide members 8 and 10 are configured to spirally surround the heater 6. The width of the fluid guide members 8 and 10 is formed to be greater than that of the heater 6. As illustrated in FIG. 2, the fluid guide members 8 and the fluid guide members 10 can communicate with each other along both sides of the heater 6.

An inlet 12 and an outlet 14 through which a fluid flows in and flows out are formed in the lower plate 4 of the cartridge. The inlet 12 and the outlet 14 are illustrated as being formed in the lower plate 4 of the cartridge in FIG. 1, but the inlet and the outlet may be formed in the upper and lower plates 2 and 4 of the cartridge in separated structures.

A fluid that flows in the inlet 12 is heated while moving to the front and rear surfaces of the heater 6 through passages formed by the fluid guide members 8 and 10 and moving to the outlet 14. In such a heating process, air bubbles may be formed.

In accordance with an embodiment of the present invention, discharge ports 16 are formed as means for discharging such air bubbles by opening the space between the fluid guide members 8.

Likewise, discharge ports 18 are formed by opening the space between the fluid guide members 10.

Furthermore, air filters 20 and 22 having a size to generally cover the discharge ports are provided so that a fluid does not exit from the discharge ports 16 and 18, but only gases exit from the discharge ports 16 and 18.

Accordingly, when air bubbles are formed in a fluid heated by the heater 6, the air bubbles are discharged through the air filters 20 and 22 while the fluid moves along the fluid guide members 8 and 10.

Commonly known filters may be used as the air filters 20 and 22, and thus a detailed description thereof is omitted.

In order to fix the air filters 20 and 22 so that they do not move toward the discharge ports 16 and 18, covers 24 and 26 for pushing the air filters 20 and 22 from the outside of the cartridge to the inside thereof are provided. A plurality of holes 27 are perforated in the covers 24 and 26, and thus the air bubbles discharged through the air filters 20 and 22 can exit to atmosphere.

Seated grooves 28 and 30 in which the covers 24 and 26 and the air filters 20 and 22 may be placed are respectively formed in the upper and lower plates 2 and 4 of the cartridge. The air filters 20 and 22 and the covers 24 and 26 are placed in the seated grooves 28 and 30 and bonded together using adhesives.

The upper plate 2 of the cartridge and the lower plate 4 of the cartridge have further extended extension units 32 and 34. The extension units 32 and 34 are formed at locations where they face each other. Each of the extension units is provided with fluid flow blocking means.

If the supply of a fluid is stopped or completed and the inside of the cartridge enters a negative pressure state, external air can flow into the cartridge. Accordingly, the fluid flow blocking means provided by an embodiment of the present invention blocks the inflow of the external flow.

Furthermore, if the cartridge is placed at a location lower than the location where a person to which a fluid is supplied is placed while the fluid is supplied, the supplied fluid can flow backward. Accordingly, the fluid flow blocking means prevents the back flow of the fluid.

For such an operation, in the fluid flow blocking means according to the present embodiment, a passage H is formed in the last guide member 9 of the plurality of fluid guide members 10 so that the fluid can flow to a region S1 through the passage H.

The region S1 is restricted by an external barrier rib 36 protruded in the lower plate 4 of the cartridge. In contrast, a groove 37 into which the external barrier rib 36 may be inserted is formed in the upper plate 2 of the cartridge. Accordingly, the upper and lower plates of the cartridge can be closely coupled.

An internal barrier rib 38 is formed inside the region S1 surrounded by the external barrier rib 36 so that a fluid within the region S1 does not flow into the internal barrier rib 38.

A region S2 surrounded by the internal barrier rib 38 is configured to communicate with the outlet 14.

The external barrier rib 36 is formed in the extension unit 34 of the lower plate 4 of the cartridge. The extension unit 32 of the upper plate 2 of the cartridge is covered over the region S1 so that the region S1 is closed and sealed. A plurality of outflow passages 40 are perforated in the extension unit 32 so that a fluid within the region S1 flows out.

A discharge passage 42 for flowing a fluid to the region S2 is formed in the extension unit 32 in which the outflow passages 38 is formed.

The discharge passage 42 is perforated at the location corresponding to the region S2 communicating with the outlet 14. Accordingly, when the upper and lower plates of the cartridge are coupled, they can communicate with each other.

A film member 44 is closely placed outside the outflow passages 40 and the discharge passage 42. The film member 44 is fixed to the extension unit 32 by a fixing member 46 extended from the cover member 24.

If the film member 44 is fixed, the four sides of the film member 44 are pressed and fixed by a pressurization unit 47 protruded in the periphery of the fixing member 46.

The cover member 24 and the fixing member 46 may be individually made or integrally made. A hole 48 is perforated in the fixing member 46 so that external air can act on the film member 44.

The film member 44 is formed to have a thin thickness. A material for the film member, such as polycarbonate, may be used as a thermoplastic-series material having excellent flexibility. The film member 44 may be made of any material that is expanded by pressure, that maintains its original state when the pressure disappears, and that has a heat-resistant property and good durability.

In accordance with an embodiment of the present invention, the fluid blocking means may be installed in either one of the upper and lower plates of the cartridge, or may be provided to both the upper and lower plates.

For example, as illustrated in FIG. 1, outflow passages 41 having the same action as the outflow passages 40 may be perforated in the region S1 of the lower plate 4 of the cartridge, another film member 45 made of the same material as the film member 44 may be placed on the other side of the region S1, and a fixing member 49 may be formed in the cover 26 and coupled with the lower plate of the cartridge.

If the fluid flow blocking means is installed in both the upper plate 2 of the cartridge and the lower plate 4 of the cartridge as described above, there is an advantage in that the amount of flow of a fluid can be sufficiently secured. In this case, a hole 50 needs to be perforated in the fixing member 49 so that atmospheric pressure acts on the film member 45.

In the present embodiment, the fluid flow blocking means has been illustrated as being formed in the extension units 32 and 34 of the upper plate 2 of the cartridge and the lower plate 4 of the cartridge and the external barrier rib 36 has been illustrated as being formed in the extension unit 3 of the lower plate 4 of the cartridge, but they are not limited thereto. The height of the external barrier rib 36 may be formed at locations corresponding to the upper plate 2 of the cartridge and the lower plate 4 of the cartridge each by half and the upper plate 2 of the cartridge and the lower plate 4 of the cartridge are bonded together so that they face each other.

In the heating apparatus configured as described above in accordance with an embodiment of the present invention, a fluid (a infusion solution or blood) flows between the upper and lower plates 2 and 4 of the cartridge through the inlet 12, and flows toward the outlet 14 through the passage formed by the fluid guide members 8.

In such a process in which the fluid flows, the fluid reaches a proper injection temperature of the human body while being heated by the heater 6.

Figure 4:
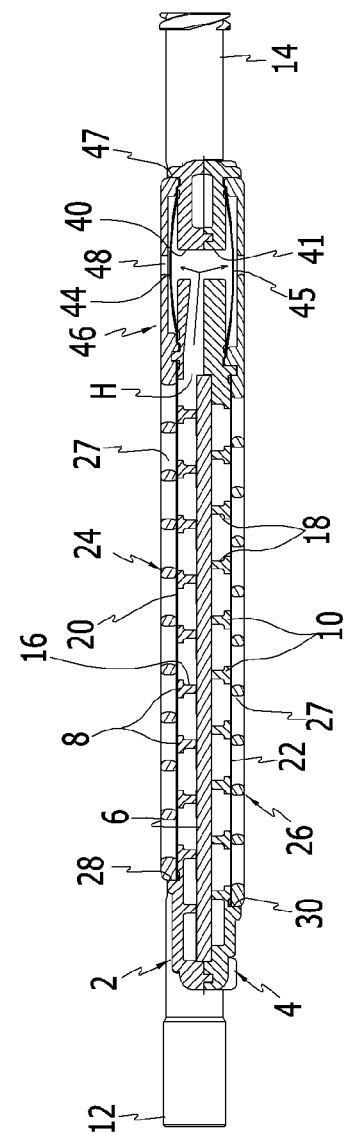
FIG. 4 is a cross-sectional view of the heating apparatus in accordance with an embodiment of the present invention, which is longitudinally taken based on the outflow passages of the heating apparatus.

In this process, air bubbles are generated in the fluid. The generated air bubbles passes through discharge ports 16 and 18 formed in the upper plate 2 of the cartridge and the lower plate 4 of the cartridge as illustrated in FIG. 4. The discharge ports 16 and 18 are respectively covered by the air filters 20 and 22, so the air bubbles generated in the fluid are discharged to atmosphere through the air filters 20 and 22.

The fluid heated as described above passes through the passage H in the state in which the air has been removed from the fluid, reaches the regions S1 respectively formed in the upper and lower plates 2 and 4 of the cartridge, and exits through the outflow passages 40 and 41 perforated in the regions.

The outsides of the outflow passages 40 and 41 are covered by the film members 44 and 45. The film members are expanded by pressure of the fluid that exits through the outflow passages 40 and 41 so that the blocked outflow passages 40 and the discharge passage 42 are connected, as illustrated in FIG. 4.

Figure 5:
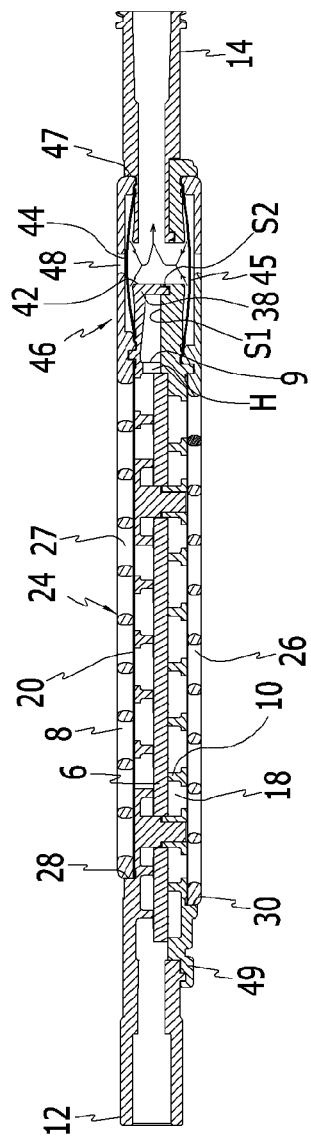
FIG. 5 is a cross-sectional view of the heating apparatus in accordance with an embodiment of the present invention, which is longitudinally taken based on the discharge passage of the heating apparatus.
Figure 6:
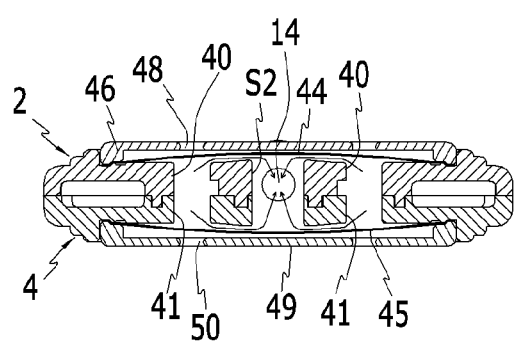
FIG. 6 is a cross-sectional view of the heating apparatus in accordance with an embodiment of the present invention, which is laterally taken based on the discharge passage of the heating apparatus.

Accordingly, the fluid flows into the discharge passage 42 through the outflow passages 40 by the expansion of the film members 44 and 45. Accordingly, the fluid can reach the passage S2 because the discharge passage 42 comes in contact with the region S2 and forms a passage through which the discharge passage 42 is connected to the region S2 as illustrated in FIGS. 4, 5, and 6.

Since the passage S2 is connected to the outlet 14, a infusion solution or blood (i.e., a fluid) of a heated state from which air bubbles have been removed can be normally supplied.

However, if the supply of a fluid is completed from such a normal fluid supply state, pressure within the passage in which the upper plate 2 of the cartridge and the lower plate 4 of the cartridge are substantially formed is reduced.

When pressure within the upper and lower plates of the cartridge becomes a negative pressure state, the medical heating apparatus according to the present invention blocks the fluid flow passage formed by the upper and lower plates of the cartridge so that external air does not flow into the human body.

Figure 7:
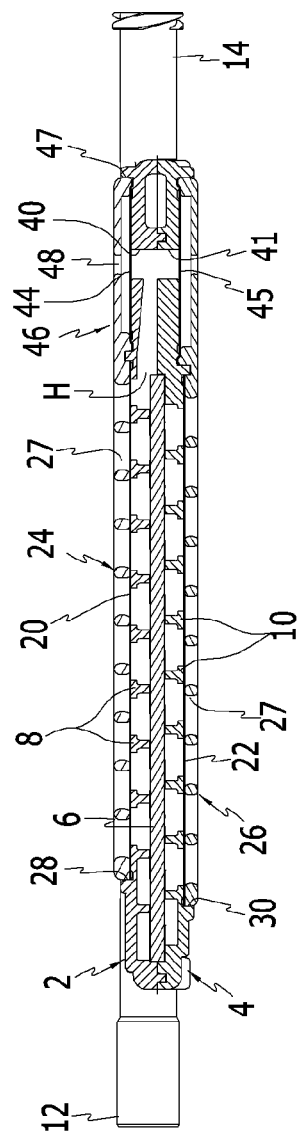
FIG. 7 is a diagram illustrating the state in which fluid flow blocking means operates in the heating apparatus of FIG. 4.
Figure 8:
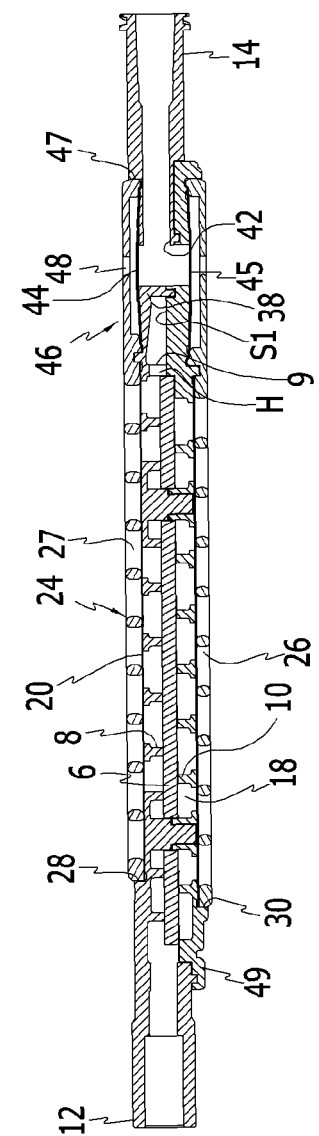
FIG. 8 is a diagram illustrating the state in which the fluid flow blocking means operates in the heating apparatus of FIG. 5.
Figure 9:
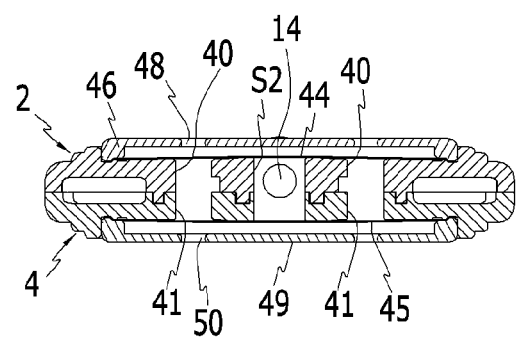
FIG. 9 is a diagram illustrating the state in which the fluid flow blocking means operates in the heating apparatus of FIG. 6.

That is, when the inside of the upper and lower plates 2 and 4 of the cartridge enters a negative pressure state, the film members 44 and 45 are restored to their original state because the expansive force of the film members 44 and 45 expanded by the flow pressure of the fluid disappears. Accordingly, as illustrated in FIGS. 7, 8, and 9, the film members 44 and 45 are closely bonded to the surfaces of the outflow passages 40 and the discharge passage 42 formed in the extension unit 32.

If the outsides of the outflow passages 40 and the discharge passage 42 are covered as described above, the fluid flow passage of the fluid flowing through the outflow passages 40 and the discharge passage 42 is blocked. Accordingly, no fluid flows.

Such a fluid flow blocking action is identically generated in the upper plate 2 of the cartridge and the lower plate 4 of the cartridge.

If a fluid changes from the normal state to the negative pressure state in the cartridge, it is immediately blocked by the expansion and restoring force of the film members.

Furthermore, such an action can prevent a back flow of a supplied fluid even if the fluid supplied to the human body flows backward because the inside of the cartridge enters the negative pressure state due to physical factors.

The invention claimed is:

1. A medical heating apparatus comprising:
   an upper plate of a cartridge in which fluid guide members for guiding a flow of a fluid are formed;
   a lower plate of the cartridge in which an inlet and an outlet are formed and other fluid guide members spaced apart from the fluid guide members formed in the upper plate of the cartridge at an interval are formed;
   a heater which is disposed between the upper and lower plates of the cartridge and that heats the fluid guided by the fluid guide members formed in the upper and lower plates of the cartridge;
   a first air filter which is placed outside the fluid guide members formed in the upper plate of the cartridge and a second air filter which is placed outside the fluid guide members formed in the lower plate of the cartridge and discharges air bubbles generated in the heated fluid to an atmosphere; and
   a fluid flow blocking means provided on fluid flow passages of the upper and lower plates of the cartridge, that normally maintains the flow of the fluid in a positive pressure state, and that blocks the flow of the fluid when a negative pressure is generated within the cartridge,
   wherein the fluid flow blocking means comprise:
   an extension unit which is formed in the upper plate of the cartridge and through which the fluid introduced through the fluid guide members formed in the upper and lower plates of the cartridge passes;
   a film member which is formed in the extension unit of the upper plate of the cartridge and closely attached to outsides of outflow passages through which the fluid is able to pass and a discharge passage which discharges the fluid drained from the outflow passages;
   an extension unit which is formed in the lower plate of the cartridge and through which the fluid introduced through the fluid guide members formed in the upper and lower plates of the cartridge passes; and
   a region which is formed in the extension unit of the lower plate of the cartridge and communicates with the outlet while communicating with the discharge passage.

2. The medical heating apparatus of claim 1, wherein the fluid flow blocking means is installed on both the upper plate of the cartridge and the lower plate of the cartridge.

3. The medical heating apparatus of claim 1, wherein a two covers, each in which a plurality of holes is formed, are provided where a first of the two covers is coupled outside the first air filter and a second of the two covers is coupled outside the second air filter.

4. The medical heating apparatus of claim 1, wherein the film member is coupled to the extension unit formed in the upper plate of the cartridge by a fixing member in which a hole is perforated.

5. The medical heating apparatus of claim 1, wherein a last guide member of the fluid guide members formed in the lower plate of the cartridge guiding the flow of the fluid is cut away to form a passage.

6. The medical heating apparatus of claim 1, wherein the film member is a thermoplastic resin-series material.

* * * * *